(12) United States Patent
Dymacek et al.

(10) Patent No.: US 10,588,892 B2
(45) Date of Patent: Mar. 17, 2020

(54) PHARMACEUTICAL COMPOSITION COMPRISING SACUBITRIL AND VALSARTAN

(71) Applicant: Synthon B.V., Nijmegen (NL)

(72) Inventors: Bohumil Dymacek, Blansko (CZ); Marta Vivancos Martinez, Sant Boi de Llobregat (ES); Luis Nogueiras Nieto, Sant Boi de Llobregat (ES); Lisardo Alvarez Fernandez, Sant Boi de Llobregat (ES); Rohit Kumar, Sant Boi de Llobregat (ES); Jose Velada Calzada, Nijmegen (NL); Petr Mitas, Blansko (CZ)

(73) Assignee: SYNTHON B.V., Nijmegen (NL)

( * ) Notice: Subject to any disclaimer, the term of this patent is extended or adjusted under 35 U.S.C. 154(b) by 0 days.

(21) Appl. No.: 16/046,531

(22) Filed: Jul. 26, 2018

(65) Prior Publication Data

US 2019/0030000 A1    Jan. 31, 2019

(30) Foreign Application Priority Data

Jul. 28, 2017   (EP) ..................... 17183859

(51) Int. Cl.
*A61K 31/41*   (2006.01)
*A61K 9/20*    (2006.01)
(Continued)

(52) U.S. Cl.
CPC ............ *A61K 31/41* (2013.01); *A61K 9/0053* (2013.01); *A61K 9/2009* (2013.01);
(Continued)

(58) Field of Classification Search
CPC .... A61K 31/225; A61K 31/41; A61K 31/216; A61K 9/0053; A61K 9/2027;
(Continued)

(56) References Cited

U.S. PATENT DOCUMENTS 5,217,996 A   6/1993  Ksander
5,399,578 A   3/1995  Bühlmayer et al.
(Continued)

FOREIGN PATENT DOCUMENTS

CN   105837464 A   8/2016
EP   0498361       8/1992
(Continued)

OTHER PUBLICATIONS

Kaplinsky, "Sacubitril/Valsartan in heart failure: latest evidence of and place in therapy," in Therapeutic Advances in Chronic Disease, a review article, 2016, pp. 278-290.*
(Continued)

*Primary Examiner* — Blessing M Fubara
(74) *Attorney, Agent, or Firm* — Buscher Patent PLLC

(57) ABSTRACT

The present invention relates to a pharmaceutical composition comprising a physical mixture of sacubitril sodium and valsartan disodium, wherein the X-ray powder diffraction pattern of valsartan disodium comprises characteristic peaks at the following 2 theta (±0.2) angles: 4.70°, 9.29°, 22.34°, measured using a Cu Kα radiation. The invention further relates to the use of said pharmaceutical composition as medicament in the treatment of heart failure.

21 Claims, 7 Drawing Sheets

(51) Int. Cl.
   *A61K 31/225*   (2006.01)
   *A61K 9/00*     (2006.01)
   *A61K 9/28*     (2006.01)
   *A61K 31/216*   (2006.01)
   *C07D 257/04*   (2006.01)

(52) U.S. Cl.
   CPC .......... *A61K 9/2013* (2013.01); *A61K 9/2027* (2013.01); *A61K 9/2054* (2013.01); *A61K 9/28* (2013.01); *A61K 31/216* (2013.01); *A61K 31/225* (2013.01); *C07D 257/04* (2013.01); C07B 2200/13 (2013.01)

(58) Field of Classification Search
   CPC ...... A61K 9/2009; A61K 9/28; A61K 9/2054; A61K 9/2013; C07D 257/04; C07B 2200/13
   See application file for complete search history.

(56) References Cited

U.S. PATENT DOCUMENTS

| | | |
|---|---|---|
| 6,204,281 B1 | 3/2001 | Webb et al. |
| 7,468,390 B2 | 12/2008 | Ksander et al. |
| 8,101,659 B2 | 1/2012 | Ksander et al. |
| 8,404,744 B2 | 3/2013 | Ksander et al. |
| 8,796,331 B2 | 8/2014 | Ksander et al. |
| 8,877,938 B2 * | 11/2014 | Feng .................... C07D 207/50 548/253 |
| 9,388,134 B2 | 7/2016 | Feng et al. |
| 2013/0319915 A1 * | 12/2013 | Gellibolian ............ C02F 1/002 210/87 |
| 2014/0073677 A1 | 3/2014 | Marti et al. |
| 2019/0083406 A1 * | 3/2019 | Winzenburg ............ A61K 9/28 |

FOREIGN PATENT DOCUMENTS

| | | |
|---|---|---|
| EP | 0 555 175 A1 | 8/1993 |
| EP | 0726072 | 8/1996 |
| WO | WO 02/06253 | 1/2002 |
| WO | WO 02/06253 A1 | 1/2002 |
| WO | WO 03/059345 | 7/2003 |
| WO | WO 2007/056546 A1 | 5/2007 |
| WO | WO 2009/061713 A1 | 5/2009 |
| WO | 2016/201238 A1 | 12/2016 |
| WO | WO 2017/012600 A1 | 1/2017 |
| WO | 2017/097275 A1 | 6/2017 |

OTHER PUBLICATIONS

Entresto Dosage disclosure, Medsacpe, Jul. 11, 2015.*
Ruilope et al., "Blood-pressure reduction with LCZ696, a novel dual-acting inhibitor of the angiotensin II receptor and neprilysin: a randomized, double-blind, placebo-controlled, active comparator study," in Lancet, vol. 375 Apr. 10, 2010, pp. 1255-1266.*
Third Party Observations concerning International Patent Application PCT/EP2018/070212 (WO2019/020706 A1) including Annexes C1-C5.

* cited by examiner

PHARMACEUTICAL COMPOSITION COMPRISING SACUBITRIL AND VALSARTAN

BACKGROUND OF THE PRESENT INVENTION

Valsartan, chemically (S)—N-(1-carboxy-2-methyl-prop-1-yl)-N-pentanoyl-N-[2'-(1H-tetrazol-5-yl)-biphenyl-4-yl-methyl]-amine of formula (II),

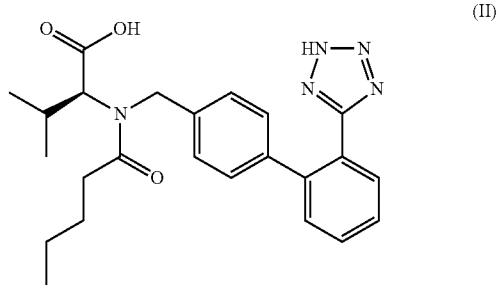 [SMILES: CCCCC(=O)N(Cc1ccc(-c2ccccc2-c2nn[nH]n2)cc1)[C@H](C(=O)O)C(C)C]

is an angiotensin receptor antagonist. It is marketed under the trade name Diovan® to treat high blood pressure, congestive heart failure and to reduce death of people with left ventricular dysfunction after having a heart attack. It is also used in combination with other pharmaceutically active compounds. Valsartan is present in Diovan® in its free acid form. WO2002006253 discloses several salts of valsartan. Examples 5 and 11 describe processes to prepare valsartan disodium.

Sacubitril, chemically (2R,4S)-5-biphenyl-4-yl-5-(3-carboxy-propionylamino)-2-methyl-pentanoic acid ethyl ester of formula (I),

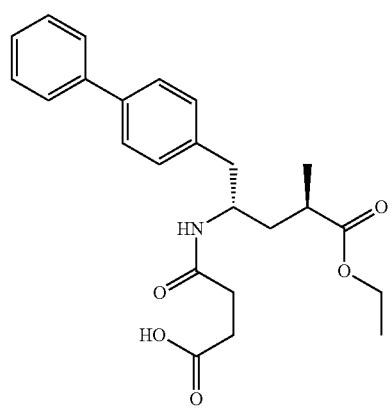

is a neutral endopeptidase inhibitor which is used in combination with valsartan.

Sacubitril is a prodrug that is activated by hydrolysis of the ester functionality. Several salts of sacubitril have been described in literature. Sacubitril sodium is disclosed in EP0555175. The process to prepare the sodium salt is described in example 1 of this application. Several polymorphic forms of sacubitril sodium are disclosed in CN105837464.

The combination drug sacubitril/valsartan is marketed by Novartis under the brand name Entresto® to treat heart failure. The fixed-dose combination product contains a co-crystal complex of the sodium salts of the two individual compounds in hydrated form. Entresto® is supplied for oral administration as immediate release film-coated tablets in three strengths: 24/26, 49/51 and 97/103 mg, containing respectively 24.3 mg sacubitril/25.7 mg valsartan, 48.6 mg sacubitril/51.4 mg valsartan and 97.2 mg sacubitril/102.8 mg valsartan. According to the information published by the EMA in the European Public Assessment Report (EPAR), the co-crystal form identified by Novartis renders valsartan more bioavailable than in its standalone formulations.

Entresto® is a BCS class IV product, having low permeability and low solubility. The drug substance is practically insoluble in water.

WO2007056546 discloses the trisodium hemipentahydrate supramolecular complex, as present in Entresto® and WO2009061713 discloses solid oral dosage forms thereof.

WO2017012600 discloses pharmaceutical compositions containing valsartan free acid, or a pharmaceutically acceptable salt thereof, sacubitril free acid, or a pharmaceutically acceptable salt thereof, and suitable excipients. In the application, several tablet compositions comprising different combinations of sacubitril free acid, its sodium, calcium or cyclohexylammonium salt with valsartan free acid, its sodium or disodium salt are described. The total amount of impurities in the compositions after storage under different conditions is given. No information regarding dissolution behavior or comparison with Entresto® tablets is made.

It would be advantageous to develop a pharmaceutical composition comprising a physical mixture of sacubitril sodium and valsartan disodium which would be bioequivalent to Entresto®. This composition should exhibit excellent long term stability and should be suitable for production on commercial scale by applying techniques and equipment commonly used in industry.

BRIEF DESCRIPTION OF THE PRESENT INVENTION

The present invention provides a pharmaceutical composition comprising a physical mixture of sacubitril sodium and valsartan disodium, wherein the X-ray powder diffraction pattern of valsartan disodium comprises characteristic peaks at the following 2 theta (±0.2) angles: 4.70°, 9.29°, 22.34°, measured using a Cu Kα radiation.

It further provides a process to prepare said composition comprising dry granulation.

Said pharmaceutical composition may be used as medicament in the treatment of heart failure.

The present invention also provides the novel polymorphic form of valsartan disodium having an X-ray powder diffraction pattern comprising characteristic peaks at the following 2 theta (±0.2) angles: 4.70°, 9.29°, 22.34°, measured using a Cu Kα radiation.

Said form of valsartan disodium may be prepared by adding at least two molar equivalents of sodium hydroxide to valsartan in a mixture of water and an alcoholic solvent, followed by addition of an anti-solvent, subsequent filtration and drying.

It also provides pharmaceutical compositions comprising said polymorphic form of valsartan disodium.

DETAILED DESCRIPTION OF THE PRESENT INVENTION

The marketed formulation of Entresto® is a fixed-dose combination containing a co-crystal complex of the sodium salts of the two individual compounds in hydrated form. The co-crystal is a trisodium hemipentahydrate complex. According to the information published by the EMA in the European Public Assessment Report (EPAR), the advantage of using the co-crystal is that the bioavailability of valsartan in the co-crystal is higher when compared with standalone formulations. As a result, the dose was reduced accordingly.

It was surprisingly found by the present inventors that a pharmaceutical composition comprising a physical mixture of sacubitril sodium and a specific polymorphic form of valsartan disodium, containing the same low dose of both active pharmaceutical ingredients as Entresto®, is bioequivalent to Novartis' product. The two active pharmaceutical ingredients, sacubitril sodium and valsartan disodium, are combined in the physical mixture while retaining their identities. The physical mixture is thus completely free of any co-crystal or other complex formed between both compounds.

Valsartan disodium is disclosed in WO2002006253. Examples 5 and 11 describe processes to prepare valsartan disodium. Example 11 provides an XRPD pattern of the valsartan disodium obtained. This polymorphic form is designated herein as "form 1". Rework of example 5 in our laboratory resulted in the isolation of amorphous valsartan disodium.

Figure 1:
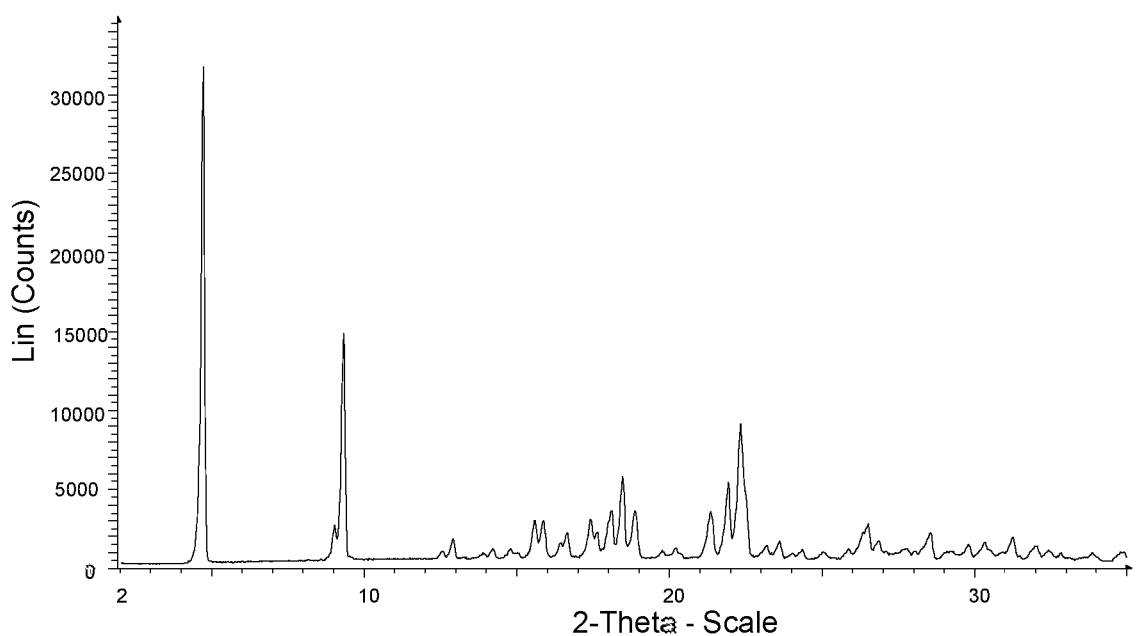
FIG. 1 shows the full X-ray powder diffraction pattern of valsartan disodium form 2 in accordance with the present invention. For measurement conditions see the Examples section.

A novel polymorphic form of valsartan disodium has been discovered by the present inventors. This novel polymorphic form of valsartan disodium is designated as "form 2" and has an X-ray powder diffraction pattern (XRPD) comprising characteristic peaks at the following 2 theta (±0.2) angles: 4.70°, 9.29°, 22.34°, measured using a Cu Kα radiation. The XRPD of valsartan disodium form 2 may further comprise characteristic peaks at the following 2 theta (±0.2) angles: 18.07°, 18.46°, 18.88°, 21.91°, measured using a Cu Kα radiation. The X-ray powder diffraction pattern may even further comprise peaks at the following 2 theta (±0.2) angles: 15.59°, 15.86°, 17.41°, 21.36°, measured using a Cu Kα radiation. The full X-ray powder diffraction pattern of valsartan disodium form 2 is depicted in FIG. 1.

The valsartan disodium of the present invention is more stable than the prior art form as described in example 11 of WO2002006253. Changes in humidity have less impact on the valsartan disodium form 2 as compared to the prior art form 1. The novel polymorphic form of valsartan disodium is particularly stable at relative humidity below 40%, at temperatures between 15 and 30° C. In addition, crystalline valsartan disodium form 2 shows better processability and has better flow properties than the crystals of prior art form 1.

The form 2 of valsartan disodium according to the present invention is prepared by adding at least 2 molar equivalents of sodium hydroxide to valsartan free acid in a mixture of water and an alcohol, followed by addition of an anti-solvent and subsequent filtration. At least 2 molar equivalents of sodium hydroxide are used to prepare valsartan disodium. Preferably, 2.0-2.5 molar equivalents of sodium hydroxide are used. The amount of water in the reaction mixture is preferably at least 2.5 molar equivalents to valsartan. This is including the amount of water formed during the salt formation, which is about 2 molar equivalents. More preferably, the amount of water in the reaction mixture is at least 2.5 molar equivalents and less than 7.5 molar equivalents, including the water formed during the reaction. By using higher amounts of water, the yield of valsartan disodium form 2 is substantially decreasing. The alcohol used in the preparation of valsartan disodium according to the present invention is preferably an aliphatic alcohol of 1-5 carbon atoms. Most preferably, the alcohol used is 2-propanol. The anti-solvent to be used in accordance with the present invention is preferably an ether or ester compound. Typical examples are t-butyl methyl ether and ethyl acetate. Most preferred anti-solvent is t-butyl methyl ether. The mixture of water and an alcohol is preferably kept at 25-40° C. Before addition of the anti-solvent, it is preferably further heated. Once the crystallization has started, the suspension is cooled, preferably to 5-15° C., and the crystals are recovered from the suspension by filtration and are subsequently dried.

Valsartan disodium form 2 may also be prepared by crystallization starting from e.g. amorphous valsartan disodium. Suitable solvents to be used in this crystallization are aliphatic esters, particularly ethyl acetate or isopropyl acetate, cyclic ethers, particularly tetrahydrofuran or 2-methyltetrahydrofuran, acetone or acetonitrile. The crystallization is preferably performed at 20-30° C. The crystals obtained are isolated by filtration and subsequently dried.

Moreover, valsartan disodium form 2 may be prepared by crystallization starting from e.g. amorphous valsartan disodium using a solvent/anti-solvent system. A particularly preferred solvent system used in this preparation is a mixture of acetone and water. A particularly preferred anti-solvent is t-butyl methyl ether. The crystallization is preferably performed at 20-30° C. The crystals obtained are isolated by filtration and subsequently dried.

The pharmaceutical composition of the present invention comprises a physical mixture of sacubitril sodium and valsartan disodium, wherein the X-ray powder diffraction pattern of valsartan disodium comprises characteristic peaks at the following 2 theta (±0.2) angles: 4.70°, 9.29°, 22.34°, measured using a Cu Kα radiation. The X-ray powder diffraction pattern of valsartan disodium form 2 may further comprise characteristic peaks at the following 2 theta (±0.2) angles: 18.07°, 18.46°, 18.88°, 21.91°, measured using a Cu Kα radiation. The X-ray powder diffraction pattern may even further comprise peaks at the following 2 theta (±0.2) angles: 15.59°, 15.86°, 17.41°, 21.36°, measured using a Cu Kα radiation. It was surprisingly found that a pharmaceutical composition comprising a physical mixture of sacubitril sodium and form 2 of valsartan disodium provides a stable product which is bioequivalent to Novartis' Entresto® product.

Valsartan disodium form 2 is easy to handle, has good flow properties and is particularly stable at relative humidity below 40%. This makes form 2 of valsartan disodium very suitable to be used in a physical mixture with sacubitril sodium, because at high relative humidities (>45% RH, at temperatures between 15 and 30° C.), the physical mixture of sacubitril sodium and valsartan disodium may convert into the co-crystal. By using valsartan disodium form 2 and by preparing the composition in an environment with relative humidity below 40%, at temperatures between 15 and 30° C., formation of the co-crystal is completely avoided.

Sacubitril sodium is disclosed in EP0555175. The process to prepare the sodium salt is described in example 1. Several polymorphic forms of sacubitril sodium are disclosed in CN105837464.

Any polymorphic form of sacubitril sodium can be used in accordance with the present invention. Preferably, the polymorphic form of sacubitril sodium is, like valsartan disodium form 2, very stable at relative humidity below 40° C., at temperatures between 15 and 30° C. Particularly preferred polymorphic forms of sacubitril sodium to be used in a composition comprising a physical mixture with valsartan disodium form 2 are sacubitril sodium form 1 and form 2. Sacubitril sodium form 1 has an X-ray powder diffraction pattern comprising characteristic peaks at the following 2 theta (±0.2) angles: 3.14°, 6.25°, 11.97°, 12.73°, 13.78°, 16.50°, 18.35°, 19.93°, 21.56°, 23.75°, 26.20°, measured using a Cu Kα radiation. Sacubitril sodium form 2 has an X-ray powder diffraction pattern comprising characteristic peaks at the following 2 theta (±0.2) angles: 5.26°, 10.52°, 10.92°, 14.78°, 16.96°, 17.17°, 17.51°, 19.92°, 20.40°, 20.81°, 22.23°, measured using a Cu Kα radiation. Both polymorphic forms 1 and 2 of sacubitril sodium are stable compounds, especially at low relative humidity, and have good processability properties. The most preferred polymorphic form of sacubitril sodium to be used with valsartan disodium form 2 in a composition in accordance with the present invention is form 1.

The pharmaceutical composition in accordance with the present invention contains 25.6 mg sacubitril sodium and 28.3 mg valsartan disodium, or 51.2 mg sacubitril sodium and 56.6 mg valsartan disodium or 102.4 mg sacubitril sodium and 113.2 mg valsartan disodium.

In a preferred embodiment the particle size distributions of both valsartan disodium and sacubitril sodium are in the same range. In this way a homogeneous blend is obtained.

Valsartan disodium in accordance with the present invention may have a particle size distribution $D_{90}$ equal to or less than 30 µm. Preferably, the $D_{90}$ of valsartan disodium is equal to or less than 15 µm. In order to prevent issues in the manufacturing process due to bad pre-blend flow properties, the particle size distribution $D_{90}$ of valsartan disodium is preferably above 5 µm.

Sacubitril sodium in accordance with the present invention may have a particle size distribution $D_{90}$ equal to or less than 50 µm. Preferably, the $D_{90}$ of sacubitril sodium is equal to or less than 25 µm. In order to prevent issues in the manufacturing process due to bad pre-blend flow properties, the particle size distribution $D_{90}$ of sacubitril sodium is preferably above 2 µm.

In a preferred embodiment, valsartan disodium form 2 of the present invention has a particle size distribution $D_{90}$ equal to or less than 30 µm, while sacubitril sodium has a particle size distribution $D_{90}$ equal to or less than 50 µm. Most preferably, the $D_{90}$ of valsartan disodium is equal to or less than 15 µm and above 5 µm, and the $D_{90}$ of sacubitril sodium is equal to or less than 25 µm and above 2 µm.

The pharmaceutical composition in accordance with the present invention comprises, besides sacubitril sodium and valsartan disodium form 2, one or more diluents, disintegrants, glidants and lubricants. The excipients to be used in accordance with the present invention are well-known and are those excipients which are conventionally used by the person skilled in the art. Depending on the dosage form chosen for the pharmaceutical composition, the person skilled in the art will be able to select suitable pharmaceutically acceptable excipients. Preferably, the pharmaceutical composition is in the form of a film-coated tablet.

The pharmaceutical composition according to the present invention comprises preferably 15-60% w/w of one or more diluents, 7-26% w/w of one or more disintegrants, 0.25-1.0% w/w of one or more glidants and 0.5-7-0% w/w of one or more lubricants, all relative to the total uncoated tablet weight.

The diluent to be used in accordance with the present invention may be any diluent known to a person of ordinary skill in the art. Particularly, the diluent to be used in accordance with the present invention is an inorganic diluent, polysaccharide, mono- or disaccharide or sugar alcohol. Microcrystalline cellulose is a particularly preferred diluent.

The disintegrant to be used in accordance with the present invention may be any disintegrant known to a person of ordinary skill in the art. Suitable disintegrants to be used in accordance with the present invention are selected from the group consisting of hydroxypropyl cellulose, croscarmellose sodium, crospovidone or sodium starch glycolate. Low substituted hydroxypropyl cellulose and/or crospovidone are particularly preferred disintegrants. More preferably, a combination of these disintegrants is used in the composition of the present invention. Most preferably, low substituted hydroxypropyl cellulose is added intragranularly and crospovidone both intragranularly and extragranularly The glidant to be used in accordance with the present invention may be any glidant known to a person of ordinary skill in the art. Colloidal silicon dioxide is a particularly preferred glidant.

The lubricant to be used in accordance with the present invention may be any lubricant known to a person of ordinary skill in the art. Magnesium stearate and/or talc are particularly preferred lubricants. More preferably, a combination of these lubricants is used in the composition of the present invention. Both lubricants are preferably applied in both the intragranular and extragranular phase.

The tablets may be optionally further coated by a film-coat. The coating serves generally for cosmetic purposes. The coating material typically has no influence on the release rate, except of an inherent short initial delay in dissolution due to the time necessary to dissolve the coat.

The coating may be selected from amongst one or more of those suitable coating materials known in the art. The coating used in accordance with the present invention may comprise hydroxypropyl methylcellulose as polymer and triacetin as plasticizer or polyvinyl alcohol as polymer and macrogol as plasticizer. Preferably, it comprises hydroxypropyl methylcellulose and triacetin. Most preferably, it comprises polyvinyl alcohol as polymer and macrogol as plasticizer.

The coating may be performed by applying one or more film forming polymers, with or without other pharmaceutically inert excipients, as a solution/suspension. Coating is done using any conventional coating technique known in the art, such as spray coating in a conventional coating pan or fluidized bed processor; or dip coating.

The pharmaceutical composition in accordance with the present invention exhibits a dissolution rate of at least 50% in 15 minutes and at least 85% in 30 minutes when tested in 900 ml phosphate buffer pH 6.8 in a USP apparatus II (paddles) at 50 rpm, 37° C.

The pharmaceutical composition of the present invention is preferably packaged in blister pack material. Particularly preferred blister pack material to be used in accordance with the present invention is cold forming blister packs. Cold forming blister packs, also known as aluminum/aluminum blister packs, adopt cold forming aluminum film and lidding material of aluminum foil. The use of aluminum offers a nearly complete barrier for moisture, allowing an extended product expiration date. After storage of the pharmaceutical composition of the present invention for 6 months at 40° C./75% RH, XRPD analysis showed that valsartan disodium was kept in form 2 and did not convert into any other polymorphic form. The polymorphic form of sacubitril sodium did also not change after storage under accelerated conditions. No co-crystal formation was observed.

The pharmaceutical composition of the present invention exhibits excellent long term stability. Moreover, the pharmaceutical composition of the present invention is very suitable for production on commercial scale making use of equipment and techniques commonly used in industry.

The pharmaceutical composition of the present invention is obtained by a process comprising dry granulation by either slugging or roller compaction. It is a reliable, robust and fast process. The tablets are preferably manufactured in an environment with relative humidity below 40%, at temperatures between 15 and 30° C.

The pharmaceutical composition in accordance with the present invention may be used as a medicament. The pharmaceutical composition typically may be used in the treatment of heart failure.

The following examples are intended to illustrate the scope of the present invention but not to limit it thereto.

EXAMPLES

The full XRPD pattern of valsartan disodium form 2 of FIG. 1 was obtained using a Bruker-AXS D8 Vario diffractometer with θ/2θ geometry (reflection mode), equipped with a Lynxeye detector and applying the following measurement conditions:

Start angle (2θ): 2.0°
End angle (2θ): 35.0°
Scan step width: 0.02°
Scan step time: between 0.2-2.0 seconds
Radiation type: Cu
Radiation wavelengths: 1.5406 Å (Kα1), primary monochromator used
Exit slit: 6.0 mm
Focus slit: 0.2 mm
Divergence slit: Variable (V20)
Antiscatter slit: 11.8 mm
Receiving slit: 20.7 mm Example 1

Pharmaceutical Composition Comprising Sacubitril Sodium Form 1 and Valsartan Disodium Form 2

The film-coated tablets comprising sacubitril sodium form 1 and valsartan disodium form 2 have the composition as given in table 1.

TABLE 1

| Component | 24/26 mg | | 49/51 mg | | 97/103 mg | |
|---|---|---|---|---|---|---|
| | mg | % | mg | % | mg | % |
| Intragranular components | | | | | | |
| Sacubitril sodium | 25.598[1] | 12.80 | 51.196 | 25.60 | 102.392 | 25.60 |
| Valsartan disodium | 28.294[2] | 14.15 | 56.589 | 28.29 | 113.177 | 28.29 |
| Microcrystalline cellulose | 94.108 | 47.05 | 40.215 | 20.11 | 80.431 | 20.11 |
| Hydroxypropyl cellulose | 25.000 | 12.50 | 25.000 | 12.50 | 50.000 | 12.50 |
| Crospovidone | 14.000 | 7.00 | 4.000 | 2.00 | 8.000 | 2.00 |
| Colloidal silicon dioxide | 1.000 | 0.50 | 1.000 | 0.50 | 2.000 | 0.50 |
| Talc | 1.500 | 0.75 | 1.500 | 0.75 | 3.000 | 0.75 |
| Magnesium stearate | 3.000 | 1.50 | 3.000 | 1.50 | 6.000 | 1.50 |
| Extragranular components | | | | | | |
| Crospovidone | 4.000 | 2.00 | 14.000 | 7.00 | 28.000 | 7.00 |
| Talc | 0.500 | 0.25 | 0.500 | 0.25 | 1.000 | 0.25 |
| Magnesium stearate | 3.000 | 1.50 | 3.000 | 1.50 | 6.000 | 1.50 |
| Total core tablet weight | 200.000 | 100.00 | 200.000 | 100.00 | 400.000 | 100.00 |
| Opadry[3,4] | 6.000 | 3.00 | 6.000 | 3.00 | 12.000 | 3.00 |
| Water, purified | q.s. | q.s. | q.s. | q.s. | q.s. | q.s. |
| Coated tablet weight | 206.000 | 103.000 | 206.000 | 103.00 | 412.000 | 103.00 |

[1] Equals 24.3 mg sacubitril free acid
[2] Equals 25.7 mg valsartan free acid
[3] 24/26 mg strength: this Opadry is a combination of 40.000% (w/w) polyvinyl alcohol-partially hydrolyzed, 25.000% titanium dioxide, 20.200% (w/w) macrogol/polyethylene glycol, 14.800% (w/w) talc
[4] 49/51 mg and 97/103 mg strength: this Opadry is a combination of 40.000% (w/w) polyvinyl alcohol-partially hydrolyzed, 24.760% titanium dioxide, 20.200% (w/w) macrogol/polyethylene glycol, 14.800% (w/w) talc, 0.120% iron oxide red and 0.120% iron oxide yellow Sacubitril sodium form 1, valsartan disodium form 2, microcrystalline cellulose, low substituted hydroxypropyl cellulose, crospovidone, colloidal silicon dioxide and talc were sieved and mixed using a diffusion mixer. The intragranular magnesium stearate was sieved, added to the blend and mixed in the diffusion mixer. Dry granulation was performed by using a roller compactor. The resulting product was screened through a mesh sieve. The resulting ribbons were milled through a impactmill. The extragranular crospovidone and talc were sieved and mixed with the granulate in a diffusion mixer. The extragranular magnesium stearate was sieved and mixed with the blend in the diffusion mixer. The resulting homogeneous blend was compressed on a tablet press. The tablets were coated with a water suspension of Opadry until a weight gain of about 3%. The tablets were packed in cold forming blister packs.

The whole process was carried out in an environment with relative humidity below 40%, at temperatures between 15 and 30° C.

XRPD analysis performed after storing the tablets for 6 months at 40° C./75% RH showed that sacubitril sodium is present in crystalline form 1, while valsartan disodium is still present in the composition in form 2. No co-crystal formation was observed.

Figure 2A:
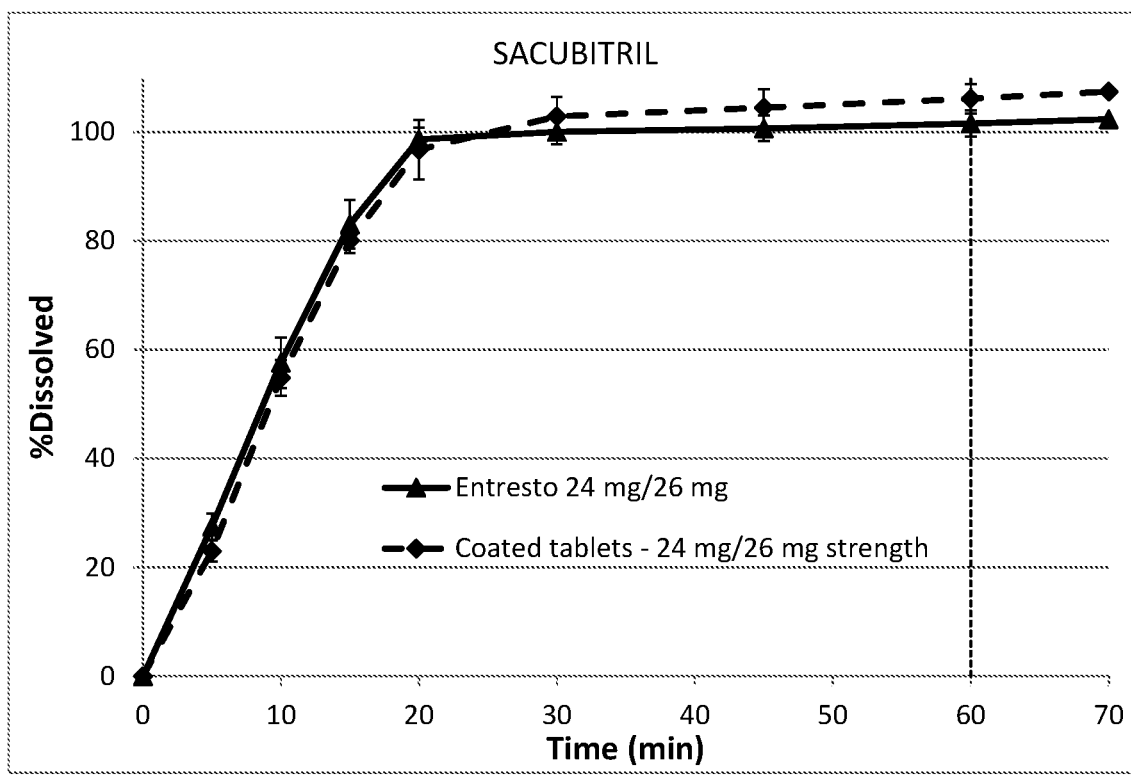
FIGS. 2A and 2B show the sacubitril and valsartan dissolution profiles, respectively, of the 24/26 mg tablet of Example 1 compared to Entresto® using USP II, 50 rpm, 900 ml, 37° C., phosphate buffer pH 6.8.
Figure 2B:
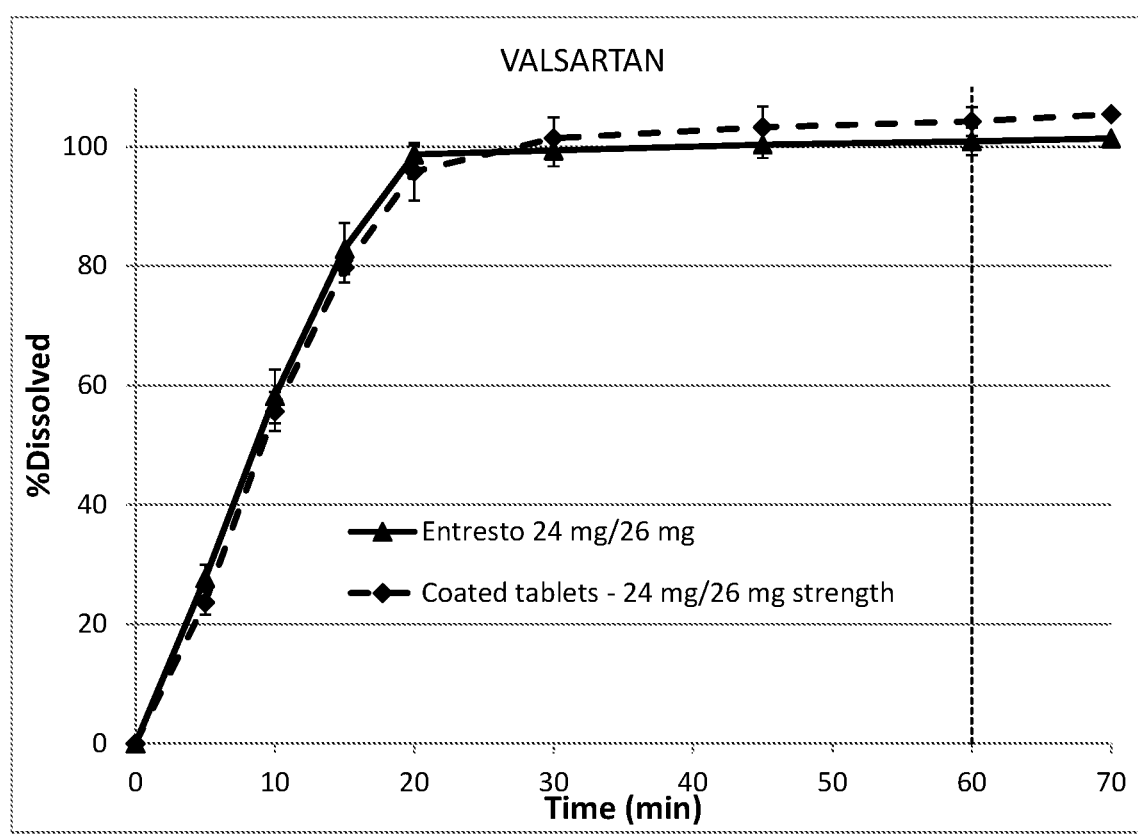
Figure 3A:
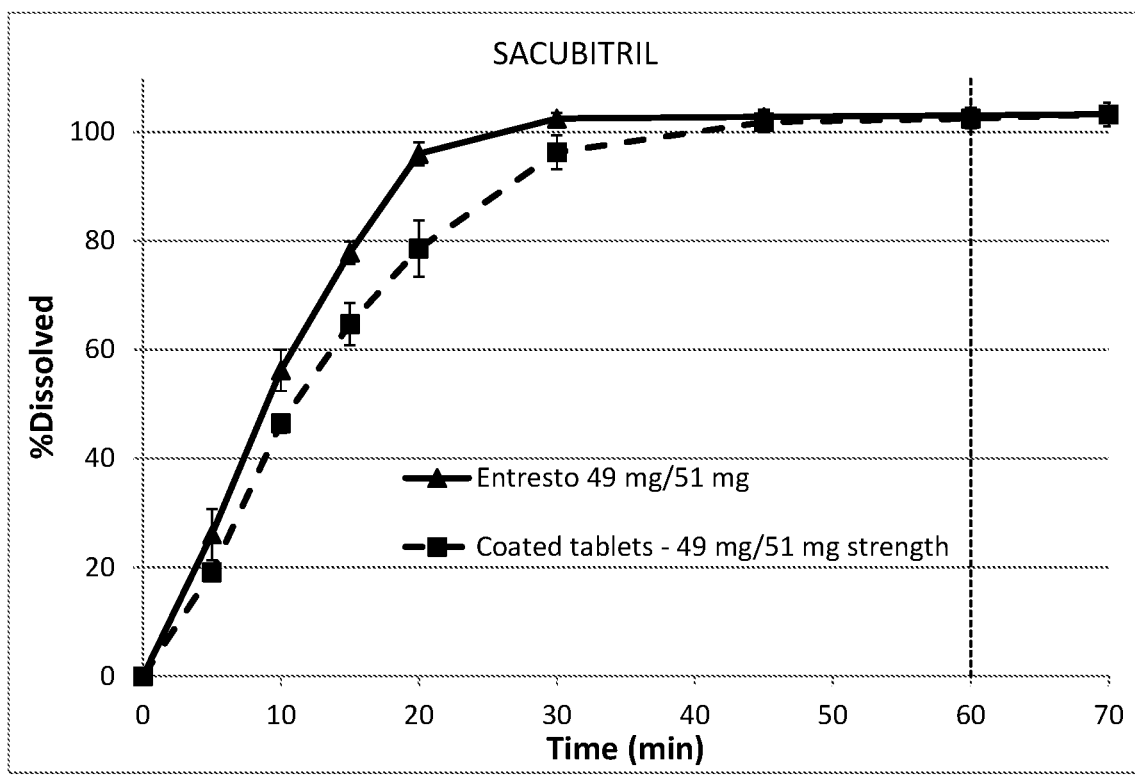
FIGS. 3A and 3B show the sacubitril and valsartan dissolution profiles, respectively, of the 49/51 mg tablet of Example 1 compared to Entresto® using USP II, 50 rpm, 900 ml, 37° C., phosphate buffer pH 6.8.
Figure 3B:
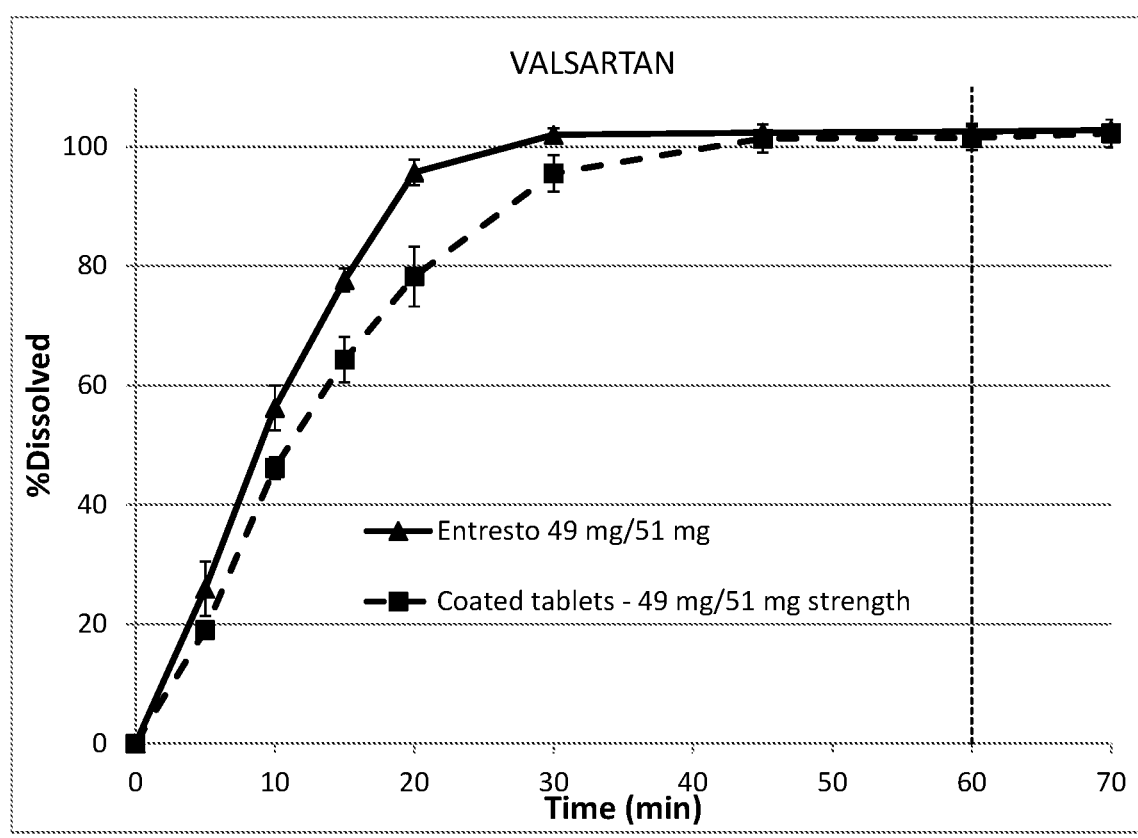
Figure 4A:
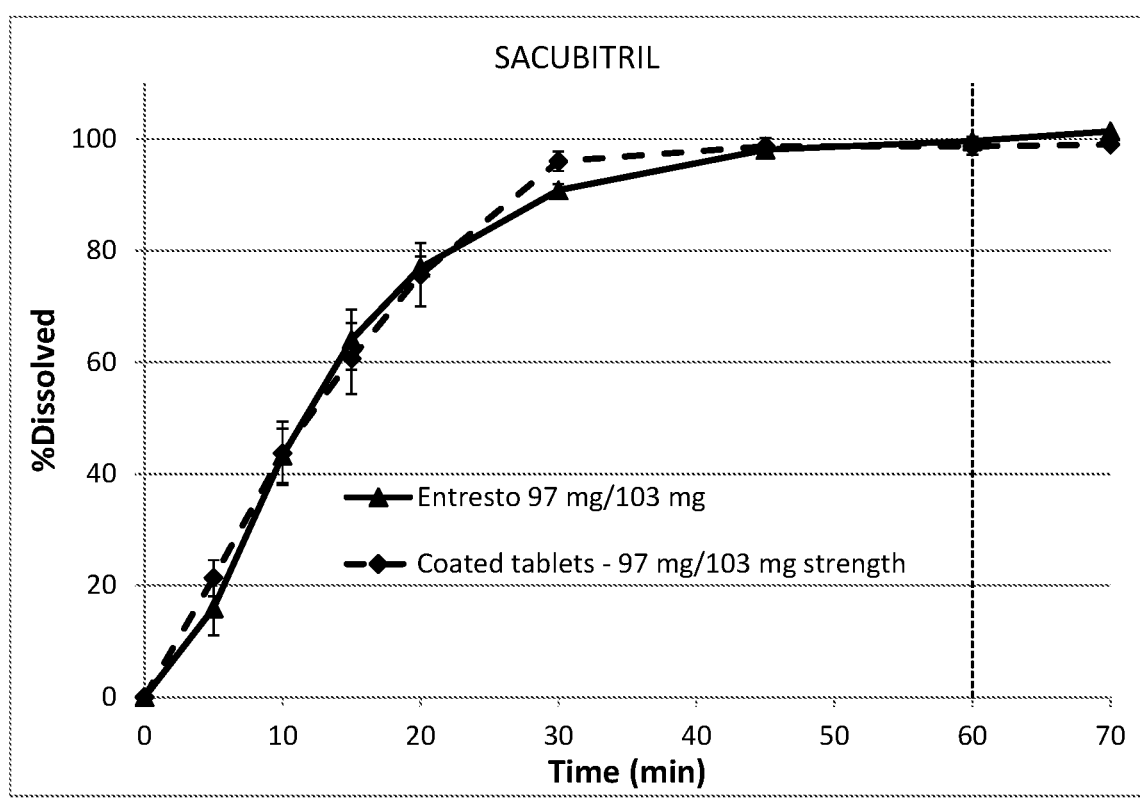
FIGS. 4A and 4B show the sacubitril and valsartan dissolution profiles, respectively, of the 97/103 mg tablet of Example 1 compared to Entresto® using USP II, 50 rpm, 900 ml, 37° C., phosphate buffer pH 6.8.
Figure 4B:
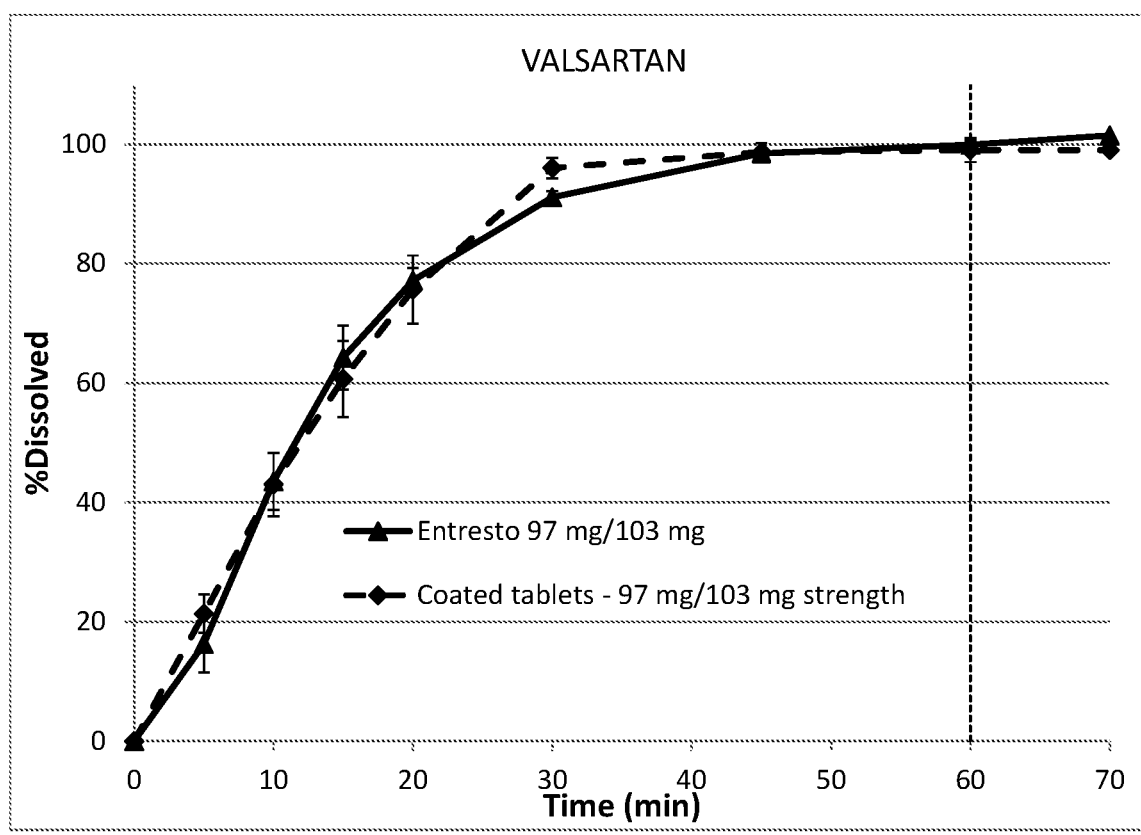

The tablets obtained, exhibited a dissolution rate of at least 50% in 15 minutes and at least 85% in 30 minutes when tested in 900 ml phosphate buffer pH 6.8 in a USP apparatus II (paddles) at 50 rpm, 37° C. The dissolution profiles of the tablets are similar to the profiles of Entresto®. The dissolution profiles of the different strengths of tablets are displayed in FIGS. 2-4.

The tablets obtained are bioequivalent to the Entresto® tablets.

Example 2

Preparation of Valsartan Disodium Form 2

A solution of sodium hydroxide (84.7 g) in water (90.0 g) was added to a solution of valsartan (450.0 g) in propanol (530 g). The resulting solution was stirred for 10 minutes at 35° C. t-Butyl methyl ether (2960 g) was added and the mixture was stirred at about 50° C. After the crystallization started, the mixture was cooled to 10° C. and was kept at this temperature for 15 minutes. The solid was isolated by filtration under vacuum, washed with t-butyl methyl ether and dried under vacuum. Valsartan disodium (404.0 g) was isolated as white to off-white solid. Analysis by X-ray powder diffraction showed that the obtained solid is valsartan disodium form 2. The X-ray powder diffraction pattern of the product is depicted in FIG. 1.

Example 3

Preparation of Valsartan Disodium Form 2

Amorphous valsartan disodium (30 mg) was dissolved at 25° C. in a solvent (150 μl) selected from ethyl acetate, isopropyl acetate, acetone, 2-methyltetrahydrofuran and acetonitrile. The obtained solution was kept at 25° C. The obtained suspension was filtered and the solid isolated was dried at 40° C. for 10-14 hours. Analysis by X-ray powder diffraction showed that the obtained solid is valsartan disodium form 2.

Example 4

Preparation of Valsartan Disodium Form 2

Amorphous valsartan disodium (60.0 g) was dissolved in acetone (150 ml) and water (5 ml). The reaction mixture was seeded with crystals of valsartan disodium form 2 and then diluted at 25° C. with t-butyl methyl ether (600 ml). After 14 hours of stirring, the suspension was filtered and the filter cake was washed with t-butyl methyl ether (50 ml), dried (130 mbar, 40° C., nitrogen flow, 12 hours). The obtained solid (59.1 g) was analyzed by X-ray powder diffraction. The analysis showed that form 2 of valsartan disodium was obtained.

The invention claimed is:

1. A pharmaceutical composition comprising a physical mixture of sacubitril sodium and valsartan disodium, wherein the X-ray powder diffraction pattern of valsartan disodium comprises characteristic peaks at the following 2 theta (±0.2) angles: 4.70°, 9.29°, 22.34°, measured using a Cu Kα radiation.

2. The composition according to claim 1, wherein the X-ray powder diffraction pattern of sacubitril sodium comprises characteristic peaks at the following 2 theta (±0.2) angles: 3.14°, 6.25°, 11.97°, 12.73°, 13.78°, 16.50°, 18.35°, 19.93°, 21.56°, 23.75°, 26.20°, measured using a Cu Kα radiation.

3. The composition according to claim 1 containing one of the following combinations of amounts:
   (i) 25.6 mg sacubitril sodium and 28.3 mg valsartan disodium;
   (ii) 51.2 mg sacubitril sodium and 56.6 mg valsartan disodium; or
   (iii) 102.4 mg sacubitril sodium and 113.2 mg valsartan disodium.

4. The composition according to claim 1, wherein valsartan disodium has a particle size distribution $D_{90}$ equal to or less than 30 μm.

5. The composition according to claim 1, wherein sacubitril sodium has a particle size distribution $D_{90}$ equal to or less than 50 μm.

6. The composition according to claim 1 further comprising one or more diluents, disintegrants, glidants and lubricants; and wherein said composition is in the form of a tablet.

7. The composition according to claim 6, wherein the diluent is microcrystalline cellulose.

8. The composition according to claim 6, wherein the disintegrants are low substituted hydroxypropyl cellulose and crospovidone.

9. The composition according to claim 6, wherein the glidant is silicon dioxide.

10. The composition according to claim 6, wherein the lubricants are talc and magnesium stearate.

11. The composition according to claim 6 that exhibits a dissolution rate for each of said valsartan and sacubitril of at least 50% in 15 minutes and at least 85% in 30 minutes when tested in 900 ml phosphate buffer pH 6.8 in a USP apparatus II (paddles) at 50 rpm, 37° C.

12. The composition according to claim 6, wherein the composition is in the form of a film-coated tablet.

13. The composition according to claim 6, wherein the tablets are packed in cold forming blister packs.

14. A process to prepare the composition according to claim 1, which comprises dry granulating sacubitril sodium and valsartan disodium form 2 to form said physical mixture.

15. The process according to claim 14, wherein the composition is prepared in an environment with relative humidity below 40%, at temperatures between 15 and 30° C.

16. A method for the treatment of heart failure, which comprises administering a composition according to claim 1 to a patient in need thereof.

17. Valsartan disodium having an X-ray powder diffraction pattern comprising characteristic peaks at the following 2 theta ((±0.2) angles: 4.70°, 9.29°, 22.34°, measured using a Cu Kα radiation.

18. A process to prepare valsartan disodium according to claim 17, comprising addition of at least 2 molar equivalents of sodium hydroxide to valsartan in a mixture of water and an alcoholic solvent, followed by addition of an anti-solvent, subsequent filtration and drying.

19. The process according to claim 18, wherein the alcoholic solvent is 2-propanol.

20. The process according to claim 18, wherein the anti-solvent is t-butyl methyl ether.

21. Pharmaceutical composition comprising valsartan disodium according to claim 17.

* * * * *